United States Patent
Petitte et al.

(10) Patent No.: US 6,515,199 B1
(45) Date of Patent: Feb. 4, 2003

(54) GENE TRANSFER IN POULTRY BY INTRODUCTION OF EMBRYO CELLS IN OVO

(75) Inventors: James Petitte, Raleigh, NC (US); Catherine A. Ricks, Raleigh, NC (US); Sally E. Spence, Frederick, MD (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 08/446,021

(22) Filed: May 19, 1995

Related U.S. Application Data

(63) Continuation of application No. 07/999,398, filed on Jan. 21, 1993, now abandoned, which is a continuation-in-part of application No. 07/826,030, filed on Jan. 27, 1992, now abandoned.

(51) Int. Cl.$^7$ .................... A01K 67/027; A01K 67/033; A01K 67/00; C12N 15/00
(52) U.S. Cl. ............................. 800/19; 800/13; 800/24
(58) Field of Search ............................. 800/2, DIG. 1, 800/13, 19, 24; 435/172.3, 240.1

(56) References Cited

U.S. PATENT DOCUMENTS 5,162,215 A    11/1992   Bosselman et al. ........... 800/23

FOREIGN PATENT DOCUMENTS

| GB | 2223755 A | 9/1988 |
| WO | WO 90/03439 | 4/1990 |
| WO | WO 90/11092 | 10/1990 |

OTHER PUBLICATIONS

Pettite et al (1990) Development 108, 185–189.*
Robertson et al (1986) Nature 322, 445–448.*
Thesis of F. Flamant, "*Utilisation de vecteurs dérivés du virus de l'Erythroblastose aviaire (AEV) pour le transfert de gènes chez les embryons de poulet*", pp. 14–34, Figs. 15 & 16 (1996).
Hua Lin et al., *Expression of Recombinant Genes in Myocardium In Vivo After Direct Injection of DNA Circulation* 82, 2217–2221 (1990).
P.B. Antin et al. *Transgene Expression in the QM Myogenic Cell Line Development Biology*, 143, 122–129 (1991).
Yuko Ando et al., *Develop., Growth and Differ.* 25, 345–352 (1983) *Ultrastructural Evidence that Chick Primordial Germ Cells Leave the Blood–Vascular System Prior to Migrating to the Gonadal Anlagen*.
Robert A. Bosselman, et al., *Science 243*, 533–535 (1989) *Germline Transmission of Exogenous Genes in the Chicken*.
C. L. Brazolot, et al., *Molecular Reproduction and Development 30*, 304–312 (1991) *Efficient Transfection of Chicken Cells by Lipofection, and Introduction of Transfected Blastodermal Cells Into the Embryo*.
Andy Coghlan, *New Scientist* 19 (Oct. 31, 1992).
Elisabeth Dupin, *Developmental Biology 105*, 288–299 (1984) *Cell Division in the Ciliary Ganglion of Quail Embryos in Situ and after Back–Transplantation into the Neural Crest Migration Pathways of Chick Embryos*.
R.S. Goldstein, et al., *Proc. Natl. Acad. Sci 87*, 4476–4480 (1990). *The microenvironment created by grafting rostral half–somites is mitogenic for neural crest cells*.
M. Bagnall et al., *Development 107*, 931–943 (1989). *The contribution made by cells from a single somite to tissues within a body segment and assessment of their integration with similar cells from adjacent segments*.
E. G. Nabel et al., *Science 249*, 1285–1288 (1990). *Site–Specific Gene Expression in Vivo by Direct Gene Transfer into the Arterial Wall*.
D.W. Salter et al., *Virology 157, 236–240 (1987)*. *Transgenic Chickens: Insertion of Retroviral Genes into the Chicken Germ Line*.
D. W. Salter et al., *Symposium*, 1445–1458 (1985). *Gene Insertion into the Chicken Germ Line by Retroviruses*.
R. M. Shuman et al., *Symposium*, 1437–1444 (1985). *Gene Transfer by Avian Retroviruses*.
K. Simkiss et al., *Protoplasma 151*, 164–166 (1989). *Transfer of primordial germ cell DNA between embryos*.
L.M. Souza et al., *The Journal of Experimental Zoology 232*, 465–473 (1984). *Application of Recombinant DNA Technologies to Studies on Chicken Growth Hormone*.
B.C. Wentworth et al., *Poultry Science Assoc.* 999–1010 (1989). *Manipulation of Avian Primordial Germ Cells and Gonadal Differentiation*.
J.A. Wolff et al., *Science 247*, 1465–1468 (1990) *Direct Gene Transfer into MNouse Muscle in Vivo*.

\* cited by examiner

*Primary Examiner*—Deborah Crouch
(74) *Attorney, Agent, or Firm*—Myers Bigel Sibley & Sajovec, P.A.

(57) ABSTRACT

A method of altering the phenotype of a bird comprises introducing a DNA sequence into somatic cells of a bird contained within an egg during in ovo incubation. The DNA sequence is selected to be effective to cause a change in phenotype, such as an increase in growth rate, feed efficiency, or both in the bird after hatch. A DNA sequence may further be selected to increase disease resistance or induce disease prevention by the expression of an antigen over a period of time.

31 Claims, No Drawings

GENE TRANSFER IN POULTRY BY INTRODUCTION OF EMBRYO CELLS IN OVO

RELATED APPLICATIONS

This is a continuation of copending application Ser. No. 07/999,398 filed on Jan. 21, 1993; now abandoned which is a continuation-in-part of U.S. patent application Ser. No. 07/826,030, filed Jan. 27, 1992 now abandoned, the content of which is herein incorporated by reference in its entirety.

FIELD OF THE INVENTION

This invention relates to the methods of altering the phenotype of birds by introducing avian embryo cells into an egg containing the bird prior to hatch, which embryo cells carry heterogenous genetic material.

BACKGROUND OF THE INVENTION

Commercial poultry is an extremely important source of food. However, there has been comparatively little attention given to methods of producing useful changes in the phenotype of birds through genetic engineering techniques. This is unfortunate, because such techniques offer a much more rapid technique for introducing desirable phenotypic traits into birds than classical breeding techniques.

Currently, the most widely investigated method of gene transfection in poultry employs retroviral vectors. Exemplary is Souza et al., *J. Exptl. Zool.* 232, 465–473 (1984), in which a retroviral vector encoding growth hormone was injected into the vascularized portion of the yolk sac of 9 day old embryos. See also Shuman and Shoffer, *Poult. Sci.* 65, 1437–1444 (1986): Salter et al., *Poultry Sci.* 65, 1445–1468 (1986); Salter et al., *Virology* 157, 236–240 (1987); Bosselman et al., *Science* 243, 533–535 (1989); and U.S. Pat. No. 5,162,215 to Bosselman et al.

Nabel et al., *Science* 249 1285–1288 (1990), and Wolff et al., *Science* 247, 1445–1468 (1990), state that transient expression of 2–5 months may be obtained from direct microinjection of DNA, but do not suggest how these techniques may be applied to genetically engineering poultry. Nabel et al. note that the expression of DNA encoding β-galactosidase injected into porcine arterial segments was limited to the microinjection site. Acsadi et al., *New Biologist* 3, 71–81 (1991) state that myocardial cells were able to transiently express injected foreign genes.

Simkiss et al., *Protoplasma* 151, 164–166 (1989) indicate that primordial germ cells of Stage XVII embryos containing endogenous retroviral sequences can be transferred to comparable recipient Stage XVI embryos that lack the retroviral marker by cardiac puncture. At day 17 of incubation, dot blots on recipient birds showed donor DNA to be present in the gonads, and traces of donor DNA to be present in the liver and heart tissues. The expression of the injected DNA molecules was not reported.

PCT Patent Application Serial No. US90/01515 discloses a method of delivering a nucleic acid sequence to the interior of a vertebrate cell. Injection of a DNA molecule into poultry was not reported.

In view of the foregoing, an object of the present invention is to provide methods of changing the phenotype of birds through genetic engineering procedures.

An additional object of the present invention is to provide a method of changing the phenotype of birds in which expression of an exogenous DNA sequence is sufficient produce the phenotypic change.

Another object of the present invention is to provide a method of changing the phenotype of birds which is rapid and convenient.

SUMMARY OF THE INVENTION

A first aspect of the present invention is a method of altering the phenotype of a bird. The method comprises introducing a DNA sequence into somatic cells of a bird contained within an egg during in ovo incubation, with the DNA sequence being effective to cause a change in phenotype in said bird after hatch (e.g., a change in growth rate, feed efficiency, disease resistance, or a combination of all of these factors). Introduction of the DNA may be carried out by any suitable means, including injecting the DNA sequence in ovo into any compartment of the egg including the body of the embryo. Preferably, the egg into which the DNA is introduced is incubated to hatch, and the bird so produced raised to at least an age at which the change in phenotype is expressed.

In an illustrative embodiment of the foregoing, the DNA sequence is introduced by first transfecting avian hematopoietic progenitor cells with the DNA sequence in vitro, and then injecting said transfected hematopoietic progenitor cells into the egg, preferably into the yolk sac or onto the chorioallantoic membrane, and preferably during early embryonic development.

A second aspect of the present invention is a method of altering the phenotype of a bird comprising introducing avian somatic tissue-specific stem cells to an egg containing a bird during in ovo incubation, wherein the avian somatic tissue-specific stem cells contain and are capable of expressing at least one DNA molecule in an amount effective to cause a change in the phenotype of the bird. Introduction of hematopoietic stem cells is a preferred embodiment, as it has been demonstrated that a DNA molecule contained therein persists and can express the protein encoded therefor at the introduction site, the bone marrow, and in the peripheral blood of the embryo. It is also preferred that the somatic tissue-specific stem cell be introduced to the bird during a developmental stage at which the cells responsible for the phenotypic expression desired to be altered are colonizing within the target tissue.

A third aspect of the present invention is a method of altering the phenotype of a bird comprising introducing avian embryo cells to the air cell of an egg containing a bird during in ovo incubation, wherein the avian progenitor cells contain and are capable of expressing at least one DNA molecule in an amount effective to cause a change in the phenotype of the bird. The inventors have demonstrated that embryo cells introduced into the air cell migrate across the air cell membrane and colonize the appropriate target tissue. Preferred cell types are embryonic stem cells and primordial germ cells.

A fourth aspect of the present invention is a method of altering the phenotype of a bird comprising introducing avian somatic tissue-specific stem cells to the air cell of an egg containing a bird during in ovo incubation, wherein the avian somatic tissue-specific stem cells containing and capable of expressing at least one DNA molecule in an amount effective to cause a change in the phenotype of the bird. Preferred cells for introduction are hematopoietic stem cells and neural crest stem cells.

A fifth aspect of the present invention is a bird produced by the foregoing methods.

A sixth aspect of the present invention is the use of a DNA sequence for the preparation of a medicament for producing a phenotypic change in a bird by introducing the medicament in ovo, as described above.

A seventh aspect of the present invention is an apparatus for the introduction of a DNA sequence in an egg during in ovo incubation, the DNA sequence capable of producing a phenotypic change in the bird carried by the egg after hatch, as described above.

DETAILED DESCRIPTION OF THE INVENTION

There are several aspects of avian embryonic development which make it an attractive target for DNA introduction by stem cell transfer. First, since the greatest period of embryonic development occurs in the egg outside the maternal reproductive tract, the embryo can be easily accessed for the introduction of exogenous DNA.

Second, the fact that the egg is a multi-compartmentalized unit can be exploited to deliver biological materials to specific embryonic sites. For example, the yolk sac in the early embryo functions to manufacture blood. Immediately prior to hatching, the yolk sac serves a primarily nutritional function and is taken into the intestinal tract and thereby transported to the cecal pouches during and after hatch. Therefore, yolk sac administration of materials can lead to both embryonic cecal or vascular system delivery. Vascular system delivery through administration of DNA into the yolk sac would be particularly desirable for administering DNA constructs capable of expressing physiologically active peptides in the bird, such as growth hormone, lymphokines such as interferon and interleukin-2, insulin-like growth factor, thyroid releasing hormone (TRH) or epidermal growth factor. In addition, administration of a peptide or DNA construct can be efficiently carried out by injection of the molecule onto the chorio-allantoic membrane or onto the air cell membrane. Finally, access to the embryonic musculature compartment can be achieved by direct embryonic injection at transfer in the last quarter of incubation, and in chickens, preferably in days 17–19 of incubation.

Third, there are several poultry embryonic cell lineages, such as blastodermal and germ cells, hematopoietic stem cells derived from aorta and yolk sac, and neural crest cells, that can be used as cellular vehicles for gene targeting.

Fourth, it is of no deleterious consequence if the transformed embryo and chicken is chimeric, so long as a physiological response is achieved in the animal after hatch sufficient to evoke the phenotypic change sought.

The foregoing and other aspects of the present invention are explained in greater detail below.

A. Phenotypic Alteration

The present invention provides a number of methods of altering the phenotype of a bird after hatch by in ovo introduction of a DNA molecule contained within a somatic stem cell or primordial germ cell to the bird. As used herein, an altered "phenotype" of a bird is intended to encompass a sustained alteration in the cellular biochemistry of a bird by the expression of a foreign DNA molecule within the tissues of the bird, which alteration results in a change in one or more physical characteristics of the bird. Thus an altered phenotype can be a change in size, appearance, endocrine response growth rate, immune response to specific antigens, metabolic rate, feed consumption and efficiency, gender, and the like. Alternatively stated, the present invention provides methods for inducing a physiological response (e.g., an immune response, or a hormonal or endocrine response) in a bird after hatch through administering to a bird in ovo a DNA molecule encoding and expressing a protein or peptide, which DNA molecule is administered in an amount effective to induce said physiological response after hatch. Note that the physiological response may be directly induced after hatch, or may be indirectly induced after hatch (such as by induction of a physiological response prior to hatch which endures after hatch), or be a constitutive expression initiated prior to hatch.

A particular altered phenotype of interest is a change in immune response wherein introduction of an avian embryo cell containing a DNA molecule immunizes the bird. Exemplary DNA molecules for introduction are those that encode a protective antigenic protein or peptide that induces an immune response from the recipient bird. This can be done in combination with or in lieu of vaccination of the bird to protect against a specific pathogen.

Altering the endogenous immune response of a bird in ovo is of particular interest due to the presence of maternal antibodies in embryonic and young mammals and birds. Maternal antibodies can interfere with typical vaccination programs for these animals. These antibodies, provided to the neonate from the bloodstream of the mother, conjugate with specific antigens and thus provide natural protection against those antigens prior to the development of immunocompetence by the neonate. Unfortunately, maternal antibodies can also hinder typical vaccination protocols; they bind to the immunogenic component of the vaccine and thus inhibit neonatal production of antibodies. The presence of maternal antibodies precludes vaccination early in the development of the neonate. Typically, multiple vaccination protocols are required so that active immunization can occur once maternal antibody levels have decreased to a sufficiently low level that they will no longer interfere with the vaccine.

A novel strategy for counteracting maternal antibody interference with vaccination is also disclosed herein. One aspect of this invention is a method of immunizing a bird comprising introducing a DNA molecule that encodes an antigen into the muscle tissue of a bird contained within an egg in ovo in an amount sufficient to neutralize maternal antibodies. Once neutralized, the maternal antibodies no longer interfere with a vaccine containing the antigen; thus such a vaccine can be used to immunize the bird. Alternatively, the DNA molecule can be introduced in an amount effective so that, upon expression, not only does the antigen neutralize maternal antibodies, but also provides an immunogen which vaccinates the bird against a specific pathogen.

The DNA molecule introduced can be any molecule that encodes an antigen that will neutralize maternal antibodies present in the bird. Exemplary antigens of interest include those produced by Marek's, infectious bronchitis, mycoplasma, avian leucosis, reovirus, pox, adenovirus, cryptosporidia, chicken anemia agent, Pasteurella species, avian influenza, Marek's MDX virus, Gumboro Disease virus, Newcastle Disease Virus (NDV), Infectious Bursal Disease Virus (IBDV), Rous sarcoma virus, *Escherichia coli,* and Eimeria species such as *Eimeria tenella* (causing coccidiosis).

The cell can be introduced by any of the methods set forth below, and can contain any of the DNA construct configurations set forth below.

It is preferred that the DNA molecule be introduced so that the antigen is expressed as or after the embryo develops immunocompetence, more preferably in the last quarter of incubation. At immunocompetence, surface antigens encoded by the DNA construct can stimulate both a B- and T-cell response, resulting in immunization before challenge by pathogens encountered in the field after hatch. The timing and the duration of the last quarter of incubation varies among different avian species due to the variation in incubation duration. For example, for chickens, the last quarter of incubation is from about day 16 to hatch; for turkeys, the last quarter is from about day 19 to hatch.

Other altered phenotypes of particular interest include modification of size, growth rate, feed efficiency, metabolic rate, endocrine response, neural system structure and function, and gender.

B. Gene Targeting

1. Stem Cell Injection

As used herein, the term "embryonic stem cell" is intended to refer to embryonic cells that are uncommitted to any differentiation path, or "totipotent"; i.e., their ultimate function in the mature bird is undetermined, as they can differentiate along any cell lineage pathway and terminally differentiate into any mature cell type. It is generally believed that embryonic stem cells exist in the embryo up to the developmental stage at which the embryo, still a blastula, comprises between about 8 and 64 cells. The term "tissue-specific stem cell" refers to an embryonic cell which is developmentally committed to a particular tissue type, but which can still differentiate into one of a plurality of cell types within the tissue (i.e., are "pluripotent"), and which retain the ability to self-renew. Exemplary tissue-specific stem cells are primoridal germ cells and somatic stem cells; somatic stem cells include, but are not limited to, hematopoietic stem cells, which differentiate to form the mature cells of the lymphocytic and myelocytic lineages, and neural crest stem cells, which differentiate to form portions of the nervous system and melanocytes. The term "non-tissue-specific stem cells" refers to self-renewing cells which are no longer totipotent, but which nonetheless are not committed to a specific tissue type. Examples of these cells include the cells comprising the ectoderm, endoderm, and mesoderm of the embryo. The term "embryo cell" is intended to encompass embryonic stem cells, non-tissue specific stem cells, and tissue-specific stem cells as defined above. Avian embryo cells (e.g., chicken, turkey, duck, goose, quail, pheasant) are preferred, and it is particularly preferred that the embryo cells be of the same species as the egg into which they are introduced. However, it is contemplated that non-avian cells (e.g., reptile, mammalian, such as bovine, ovine, procine, or murine) may also be employed.

The present invention encompasses the introduction of avian embryo cells into a bird in ovo to alter the phenotype of the bird. In one embodiment, it is preferred that the avian embryo cells be embryonic stem cells. In another embodiment, it is preferred that they be tissue-specific stem cells. In a further embodiment, it is preferred that the avian embryo cells be somatic tissue-specific stem cells, including hematopoietic stem cells, neural crest cells, and primordial germ cells.

The process of gene targeting is dependent on the ability to grow embryo cells in culture, which allows time for in vitro gene manipulation, as well as the viability of embryo cells containing the foreign DNA when placed into recipient birds. In avian species, certain donor cell types have been isolated that retain viability when injected into recipient embryos. See Etches et al., in *Avian Incubation*, Chapter 22, Butterworth Publishers (1990); Verrinder Gebbins et al., *Fourth World Congress on Genetics Applied to Livestock Production*, Edinburgh, (1990); Petitte et al., *Development* 108, 185–189 (1990)). These studies showed that blastodermal cells derived from Stage X embryos (embryo at hatch) remained viable when transferred to comparable recipient Stage X embryos.

Embryonic stem cells have been used effectively as cellular vehicles in mice as a means to produce any desired genotype (Capecchi, *TIG*, 5, 70–76 (1989)). A major advantage of using cells as vehicles for gene transfer is that the incorporation and function of the gene can be evaluated in vitro without screening vast numbers of animals. In addition, gene transfer in birds is most likely to be of value to the poultry industry if the modifications of the genome occur in a specific, site directed manner rather than by a random approach. Targeting of introduced genes to specific sites in the chromosome can be achieved using gene constructs that are capable of undergoing homologous recombination, in which exogenous and native DNA molecules recombine within regions of homology. The attraction of this approach lies in its potential for modification of endogenous genes in situ to enhance or eliminate expression, to alter tissue specificity, or to alter developmentally regulated expression.

Another donor cell type that can be effectively transferred is the primordial germ cell. Such cells can be isolated from the embryonic blood of Stage XVI embryos (55–60 hours of incubation). This is because these cells originate outside the embryo in the germinal crescent and migrate via the blood to the germinal ridge, which is the future site of the gonad. Simkiss et al., *Protoplasma* 151, 164–166 (1989) have demonstrated that primordial germ cells containing endogenous retroviral molecules can be transferred to comparable recipient Stage XVI embryos that lack this marker. The introduction of foreign DNA through primordial germ cells can lead to alteration of a number of phenotypic expressions, including gender.

Further, phenotype can be altered by the introduction of somatic tissue-specific stem cells. In particular, hematopoietic stem cells introduced in ovo can colonize the bone marrow and thereafter migrate into the peripheral blood of the embryo. Such colonization ensures long-term expression of the transferred gene. As such, this can be an effective method of increasing the plasma level of specific substances, such as growth factors, immunogens, and the like, in the bloodstream, and thereby alter the phenotype of the bird.

While the inventors do not wish to be bound by any theory offered to explain the mechanism underlying the invention, it is believed that migration of cells are usually associated with very primitive cell types such as hematopoietic stem cells and primordial germ cells. Both of these cell types originate in embryos at sites removed from their ultimate location, and migrate to the aorta, bone marrow, spleen and bursa, and the germinal ridge, respectively, at some point during embryonic development. Recent evidence in non-avian species suggests that the migration exhibited by both hematopoietic stem cells and primordial germ cells can be attributed to interactions between the c-kit receptor and its ligand, stem cell factor (also known as Mast Cell growth factor or Steel factor). It is possible that interactions between avian homologs of the c-kit receptor and stem cell factor are responsible for the migration and colonization of hematopoietic stem cells described below in the Examples. A similar mechanism would likely permit the engraftment of other self-renewing precursors of a multipotential cell lineage, particularly if the appropriate stem cell is transferred to the recipient embryo at a stage in development when that cell type normally colonizes the target tissue.

It should be noted that embryo cells, such as hematopoietic cells, that can be cultured for relatively long periods of time are advantageous in that they can be introduced to the bird at a stage of incubation where rejection or non-integration with host tissue is unlikely. As noted below, the probability of integration of foreign cells with the host is increased by introducing the cells at the stage in the developmental cycle in which such cells are colonizing target tissue.

An established avian muscle cell line has been shown suitable for introducing cloned transgenes into recipient embryonic muscle cells (Antin et al., *Devel. Biol* 143, 122–129 (1991); Antin and Ordahl, *Devel. Biol* 143, 111–121 (1991)).

2. DNA Constructs

The DNA molecule introduced in ovo is, in general, a construct contained within an embryo cell comprising a promoter functional in avian cells and a gene encoding a peptide or protein operably linked to the promoter. Preferably, the protein or peptide is physiologically active and capable of producing a phenotypic change in the bird. In general, the DNA construct may be a linear DNA molecule or a molecule carried by a vector or other suitable carrier such as liposomes, calcium phosphate, or DMSO. Vectors, as discussed below, may be plasmids, viruses (including retroviruses), and phage, whether in native form or derivatives thereof. Preferably, the DNA molecule does not contain retroviral DNA portions sufficient for integration of the infecting DNA into the chromosomal DNA of the host bird.

Illustrative of genes encoding a protein or peptide are those which encode a protein or peptide selected from the group consisting of growth hormone, thyroid releasing hormone (TRH), lymphokines such as interferon and interleukin-2, insulin-like growth factor, epidermal growth factor, and immunogenic recombinant antigens such as those produced by Marek's, infectious bronchitis, mycoplasma, avian leucosis, reovirus, pox, adenovirus, cryptosporidia, chicken anemia agent, Pasteurella species, avian influenze, Marek's MDX, Gumboro Disease virus, Newcastle Disease Virus (NDV), Infectious Bursal Disease Virus (IBDV), Rous sarcoma virus, *Escherichia coli,* and *Eimeria tenella.*

The production of cloned genes, recombinant DNA, vectors, transformed host cells, proteins and protein fragments by genetic engineering is well known. See e.g., U.S. Pat. No. 4,761,371 to Bell et al. at Col. 6 line 3 to Col 9 line 65; U.S. Pat. No. 4,877,729 to Clark et al. at Col. 4 line 38 to Col 7 line 6; U.S. Pat. No. 4,912,038 to Schilling at Col. 3 line 26 to Col. 14 line 12 (applicants specifically intend that the disclosure of these and all other patent references cited herein be incorporated herein by reference). Protocols for restriction endonuclease digestion, preparation of vectors, DNA purification and other such procedures were essentially as described in standard cloning manuals. See Sambrook et al., *Molecular Cloning, a Laboratory Manual,* (2d Ed., Cold Spring Harbor Press, New York (1989)).

A vector is a replicable DNA construct used to either amplify and/or express DNA encoding the gene of interest. A suitable expression vector will have controlling elements capable of expressing the cloned cDNA or genomic DNA placed in the correct orientation when the vector is introduced into the correct host. Such elements typically include but are not limited to a promoter region which interacts specifically with cellular proteins involved in transcription, enhancer elements which can stimulate transcription manyfold from linked heterologous promoters, a splice acceptor and/or donor molecules, and termination and polyadenylation signals. Also required is a DNA sequence for a ribosome binding site capable of permitting translation which is operably linked to the gene to be expressed.

Recently, a muscle-specific promoter has been isolated which is positioned upstream of both the skeletal muscle structural gene and the essential proximal promoter element and is operably associated with each. (Mar and Ordahl, *Proc. Natl. Acad. Sci. USA* 85, 6404–6408 (1988)). Other exemplary promoters operable in avian cells and embryo cells include promoters associated with the genes expressing skeletal actin, phosphoglycerate kinase (PGK), dihydrofolate reductase (DHFR), and chicken β-globin, promoters for hematopoietic stem cell antigens, promoters operably associated with hematopoietic transcription factors, the promoter for Herpes Virus, thymidine kinase and promoters for viral long-terminus repeats, such as Rous Sarcoma Virus.

Vectors comprise plasmids, viruses (e.g. adenovirus, cytomegalovirus), phage, and DNA fragments integratable into the host genome by recombination. The vector replicates and functions independently of the host genome.

C. Subjects and Time of Administration

The present invention may be carried out on any avian subject, including, but not limited to, chickens, turkeys, ducks, geese, quail, and pheasant. The embryo cells may be introduced in ovo at any time during incubation, the duration of which will vary depending upon the species. For example, DNA may be introduced into chicken eggs early in incubation (e.g., between about days 2 and 3 of incubation) or late in incubation (e.g., during the last quarter of incubation; i.e., between about day 16 of incubation and hatch).

It is preferred that the timing of embryo cell introduction coincide with the embryonic developmental stage in which the introduced cell colonizes in the the embryo. For example, if a hematopoietic stem cell is introduced to a chick embryo, it is preferred that it be introduced between about day 15 and day 17 of incubation, as it is during this stage that the endogenous hematopoietic stem cells of chick embryos typically colonize the bone marrow. By timing introduction thusly, the probability that the foreign cells will colonize also can be improved. Having colonized and thus being integrated with the host target tissue, the cells maintain their capacity for self-renewal and the capacity for differentiation into multiple lineages.

The somatic stem cell or primordial germ cell may be introduced into any region of the egg, including the air cell, the albumen, the chorio-allantoic membrane, the yolk sac, the yolk, the allantois, the amnion, or directly into the embryonic bird. Preferably, the cell is introduced into either the yolk sac or the air cell, with the air cell being a more preferred introduction site. The inventors have demonstrated that cells introduced to these sites can migrate to the target tissue rather than remaining with the site during development. Moreover, both the yolk sac and the air cell are located near the eggshell and thus are relatively easily accessed by injection apparatus without damage to other embryonic structures.

D. Methods of Introducing DNA into Eggs

Any suitable means may be used for introducing the DNA in ovo, including in ovo injection, high pressure spray through the egg shell, and ballistic bombardment of the egg with microparticles carrying the DNA construct.

Where in ovo injection is used the mechanism of injection is not critical, but it is preferred that the method not unduly damage the tissues and organs of the embryo or the extraembryonic membranes surrounding it so that the treatment will not decrease hatch rate. As mentioned, preferred injection sites include the yolk sac and the air cell, each of which is located near the eggshell and thus is relatively easily reached by injection apparatus without damage to other embryonic structures and without compromising the protection afforded by the eggshell. A hypodermic syringe fitted with a needle of about 18 to 26 gauge is suitable for the purpose. Depending on the precise stage of development and position of the embryo, a one-inch needle will terminate either in the fluid above the chick or in the chick itself. Yolk sac injection can be achieved by insertion of a needle to a depth of between about ½ and 1½ inches into the egg. Air cell injection can be carried out by injection at a depth of between about ⅛ and ½ inches into the large end of the egg. Those skilled in this art will appreciate that the injection depth can vary depending on the developmental stage of the embryo. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being the EMBREX INOVOJECT™ system (described in U.S. Pat. No. 4,681,063 to Hebrank), and U.S. Pat. Nos. 4,040,388, 4,469,047, and 4,593,646 to Miller. The disclosure of these references and all references cited herein are to be incorporated herein by reference. All such devices, as adapted for practicing the present invention, comprise an injector containing the DNA as described herein, with the injector positioned to inject an egg carried by the apparatus with the DNA. In addition, a sealing apparatus operatively associated with the injection apparatus may be provided for sealing the hole in the egg. after injection thereof.

The currently preferred apparatus for practicing the present invention is disclosed in U.S. Pat. No. 4,681,063 to Hebrank and U.S. Pat. No. 4,903,625 to Hebrank, the disclosure of which are incorporated herein by reference.

This device comprises an injection apparatus for delivering fluid substances into a plurality of eggs and suction apparatus which simultaneously engages and lifts a plurality of individual eggs from their upwardly facing portions and cooperates with the injection means for injecting the eggs while the eggs are engaged by the suction apparatus. The features of this apparatus may be combined with the features of the apparatus described above for practicing the present invention. Those skilled in the art will appreciate that this device can be adapted for injection into any portion of the egg by adjusting the penetration depth of the injector.

The present invention is explained further in the following non-limiting examples. In these Examples, "μL" means microliters, "mL" means milliliters, "ng" means nanograms, "μg" means micrograms, "mg" means milligrams, "cc" means cubic centimeters, "mm" means millimeters, "mM" means concentration in millimoles, "SSC" means a solution of 0.15M sodium chloride and 0.015M sodium citrate, "Tris" means a buffer solution of tri(hydroxymethyl)animomethane, "EDTA" means a solution of ethylene diamine tetraacetic acid and "° C." means degrees Celsius.

EXAMPLE 1

Injection of DNA In Ovo

Using the Embrex Inovoject™ system described above, gene transfer is accomplished by injecting 25, 50, or 100 μg of pmiwZ or pRSV-ADH DNA in 100 μL of phosphate buffered saline (PBS) into the embryo in the region defined by the amnion at day 18 of incubation. Embryos are sacrificed at 19, 20, or 21 days of incubation and muscle tissue is examined histologically for construct expression. LacZ expression is examined in living tissue using a non-toxic fluorescent substrate (ImaGene™, Molecular Probes, Inc.) or in fixed tissue using X-gal (Ueno et al., *Develop. Growth and Differ.* 30(1), 61–73 (1987)). ADH expression is examined in fixed tissues using 2-butanol (Ordahl, supra (1986)), a substrate which is specific for Drosophila ADH and cannot be used by vertebrate ADH. Therefore, endogenous expression is able to be distinguished from exogenous expression.

When a construct is expressed, the other injected embryos are allowed to hatch and are raised to 1–2 weeks of age. At various points during this time, the birds are sacrificed and the portion of muscle corresponding to the site of injection and expression in the 19–21 day embryos is analyzed for bacterial β-galactosidase or Drosophila AHD activity.

EXAMPLE 2

Introduction of Hematopoietic Progenitor Cells In Ovo

A DNA-liposome complex consists of 25–100 μg of recombinant DNA as described in Example 1 above and 100 μl Lipofectin™ (Gibco/BRL) formed into liposomes in accordance with known techniques. Aortic hematopoietic progenitor cells are cultured from dissociated aorta cells obtained from embryos at 3 days of incubation in accordance with known techniques. These cells are transfected in vitro with DNA-liposome complexes in accordance with known techniques and injected into the yolk sac or chorio-allantoic membrane of recipient chicken embryos in ovo at 2–3 days of incubation with an Inovoject™ injection apparatus (Embrex, Inc., Morrisville, N.C.). These embryos are incubated to hatch and the activity of the transgene assessed in bone marrow cultures and blood cells at various intervals post-hatch, utilizing the analytical techniques described in Example 1 above.

EXAMPLE 3

Preparation of Female Hematopoietic Stem Cells and Injection into Male Embryos Female chickens carry one W and one Z sex chromosome, while male chickens carry two Z chromosomes. The W chromosome contains a highly repetitive DNA sequence which is not found on any other chromosome. By using this W chromosome specific repeat sequence as a molecular marker, hematopoietic cells from female donor birds can be detected in male recipient birds by Polymerase Chain Reaction (PCR) techniques performed on peripheral blood samples and by in situ hybridization of W-specific labelled DNA probes to peripheral blood smears of recipient birds.

To effect the transfer of stem cells from female to male embryos, first viable 16 day embryos were removed from the eggshell. Embryos were dissected to determine the sex visually, and a small blood sample was obtained to confirm sex determination by PCR with W-chromosome specific primers. Male embryos were discarded, and female embryos were used for donors of hematopoietic cells.

The tibiotarsuses from both legs of female embryos were removed from surrounding muscle tissue, and the ends of the bones were trimmed. A 1 cc syringe containing cold sterile phosphate buffered saline (PBS) was inserted into the end of the bone, and bone marrow was eluted from the bone itself by dripping PBS through the lumen of the bone. Marrow from each donor was harvested and processed independently to minimize the chance of contamination. Cell numbers of each marrow sample were counted in a hemocytometer. The samples were centrifuged and resuspended in a volume of 100 to 500 μL for delivery to recipient birds.

A small hole was made in the eggshell housing each recipient bird, and donor cells were delivered either to the yolk sac or to the air cell membrane. Both delivery sites required that a hole be punched in the eggshell. Delivery to the air cell membrane was accomplished by dripping donor cells in PBS onto the membrane, while delivery to the yolk sac required direct penetration of the yolk sac with a needle. Holes in the eggshell were sealed by plastic wrap anchored by petroleum jelly, and the embryos were allowed to hatch.

Cells were transferred to 82 day 16 embryos: 41 embryos received donor cells on the air cell membrane, and 41 embryos received donor cells in the yolk sac. Twenty-eight of the 41 embryos receiving cells in the yolk sac hatched (68% hatch percentage), and 37 of 41 embryos receiving donor cells on the air cell membrane hatched (90% hatch percentage).

One week after injection, blood samples were obtained by puncturing the frontal sinus of the bird and collecting peripheral blood in syringes coated with 0.5 M EDTA solution (pH 8.0). Chicks were then euthanized by $CO_2$ and the sex of each was determined visually. Blood samples from males were then used in the PCR and DNA hybridization studies that follow.

EXAMPLE 4

PCR Analysis to Detect the Presence of DNA from Donor Females in the Blood of Recipient Males A 1 μL sample of recipient blood collected by the procedure of Example 3 was used in the PCR with primers specific for the W-chromosome specific repetitive sequence. The PCR analysis was carried out according to standard techniques, with a positive PCR signal indicating that female donor cells were present in male recipients. A total of 45 male chicks were analyzed by PCR. The data are shown in Table 1.

TABLE 1

Detection of W-Chromosome sequence in Male Chicks by PCR

| # chicks analyzed | Delivery of cells | | Sex as determined by PCR | | | |
|---|---|---|---|---|---|---|
| | air cell | | Female | | Male | |
| | membrane | yolk sac | Air cell | Yolk | Air cell | Yolk |
| 45 | 33 | 12 | 10 | 5 | 23 | 7 |

Of the chicks analyzed, 15 (33%) contained female-specific sequences in peripheral blood; 30 (67%) did not score positive for female sequences. Of the 15 positive animals, 10 (67%) received donor cells on the air cell membrane and 5 (33%) received donor cells in the yolk sac. The W-chromosome repeat sequence was detected in 30 percent of the male embryos injected into the air cell, and the sequence was detected in 42 percent of male embryos injected into the yolk sac. These data indicate that the sequence is capable of persisting in the bird for at least one week, and can migrate from the injection site to the peripheral blood of the bird in that time.

EXAMPLE 5

DNA Hybridization Procedure

The presence of donor hematopoietic cells in peripheral hard blood was also analyzed in situ by a hybridization assay specific for the W-chromosome repeat sequence. Blood was drawn from recipient birds as described in Example 3. Slides were pre-treated by dipping in a solution of 500 µg/mL poly-L-lysine and air-drying. Two and 5 µL samples of blood were smeared on the slides. Slides were incubated in a solution of 20 mM Tris pH 7.5, 2 mM $CaCl_2$ and 0.6/ml mg proteinase K for 15 minutes at 37° C., followed by two washes of 10 minutes each at room temperature with gentle agitation in 0.2% glycine (w/v) in PBS(−). Cells were fixed by placing slides in 4% (w/v) paraformaldehyde in PBS(−) for 10 minutes at room temperature followed by two 15 minute washes in 5 mM $MgCl_2$ in PBS(−) at room temperature. Samples were dehydrated by washing in 70% and 95% ethanol for 5 minutes each at room temperature, then were air-dried. DNA on the slides was denatured by incubation in 70% (v/v) formamide, 2×SSC pH 7.0 at 73° C. for 8 to 10 minutes. Slides were then immediately washed in 70% ethanol at −20° C. for 5 minutes, washed again for five minutes in 95% ethanol at −20° C., and air dried.

A hybridization solution was prepared containing 50% (v/v) formamide, 2×SSC pH 7.0, 10% (w/v) dextran sulfate, 1% (v/v) Tween-20, 100 ng/µL denatured salmon sperm DNA, and 0.5–1.0 ng/µL labelled W-chromosome-specific DNA probe. The W-specific probe was labelled by incorporation of digoxigenin-substituted nucleotides using a commercial kit (Boehringer Mannheim).

To effect hybridization, the hybridization solution was denatured at 73° C. for ten minutes, then both the hybridization solution and the slides were incubated at 37° C. for 5 minutes. Twenty µL of hybridization solution was placed on the slide, covered with a siliconized cover slip, and sealed with rubber cement. The slides were then incubated overnight at 37° C. in a moist environment. The following day the coverslips were removed by soaking the slides in 50% (v/v) formamide, 2×SSC pH 7.0 at 45° C. Slides were washed three times for 10 minutes each at 45° C. in 50% (v/v) formamide, 2×SSC pH 7.0, then washed three more times for ten minutes each in the 2×SSC pH 7.0 alone at room temperature.

Hybridization of the detector probe to the W-chromosome was detected using a colorimetric assay for an alkaline phosphatase-conjugated antibody specific to digoxigenin according to the manufacturer's directions (Boehringer Mannheim). Cells on the slides stained purple indicated the presence of female specific DNA sequences. All experiments included positive controls comprising slides of samples drawn from female chicks.

EXAMPLE 6

Results of DNA Hybridization Assay

After hybridization under the procedure described in Example 5, slides were scored for the presence or absence of cells containing the W-chromosome-specific repetitive sequence. Blood smears from six phenotypically male chicks receiving female donor cells were analyzed. The results are shown in Table 2 which sets forth the data by specimen number and site of delivery.

TABLE 2

Detection of W-Chromosome-specific Sequence in Male Chicks

| negative in situ | | positive in situ |
|---|---|---|
| Male by PCR | Female by PCR | Female by PCR |
| #6111 air cell | #7047 yolk sac | #500 air cell |
| | #7048 yolk sac | #6116 air cell |
| | | #7046 yolk sac |

Of the six chicks analyzed, five had scored positive for female DNA by the PCR analysis. Of these five, three indicated hybridization to W-specific probes in in-situ analysis. Blood smears from female chicks provided positive controls. Chicks scoring positive for female DNA sequences by PCR analysis, yet negative by in situ analysis may represent animals with a very low percentage of transferred donor cells present in peripheral blood. In situ analysis of greater numbers of cells from these chicks may be required to detect female donor cells.

These results indicate that transfer of genetically engineered hematopoietic stem cells in ovo represents a viable method of delivering foreign genes and the proteins encoded by these genes to birds. The data indicate that hematopoietic cells delivered to the yolk sac or to the air cell membrane in day 16 of incubation embryos can persist for up to one week post-transfer, and can be detected in the peripheral blood of post-hatch chicks. In no instance during the procedures of Examples 3–6 were donor cells administered directly into the circulatory systems of embryos. The delivery of hematopoietic stem cells to the air cell in ovo is particularly attractive in that an acceptable level of hatchability was maintained; hatchability of about 90% was observed. The ability to deliver a genetically engineered stem cell in ovo while maintaining good hatchability makes this a feasible approach to delivery of foreign genes and proteins encoded by those genes to the embryo.

The foregoing examples are illustrative of the present invention, and are not to be construed as limiting thereof. The invention is defined by the following claims, with equivalents of the claims to be included therein.

That which is claimed is:

1. A method of altering the phenotype of a bird, comprising introducing avian somatic tissue-specific stem cells into an egg containing a bird during in ovo incubation, said cells containing and capable of expressing at least one DNA molecule in an amount effective to cause a change in the phenotype of the bird.

2. A method according to claim 1, further comprising the step of transfecting said somatic tissue-specific stem cells with said DNA molecule prior to said introducing step.

3. A method according to claim 1 wherein said introducing step is carried out by injecting said somatic tissue-specific stem cells into a compartment of the egg selected from the group consisting of the air cell and the yolk sac.

4. A method according to claim 1 wherein said bird is selected from the group consisting of chickens, turkeys, ducks, geese, quail and pheasants.

5. A method according to claim 1 wherein said somatic tissue-specific stem cells are introduced in ovo during about the last quarter of incubation.

6. A method according to claim 1 wherein said somatic tissue-specific stem cells are introduced in ovo at a stage of development in which said stem cells colonize tissue of said bird.

7. A method according to claim 1, wherein said somatic tissue-specific stem cells are hematopoietic stem cells.

8. A method according to claim 1, wherein said somatic tissue-specific stem cells are neural crest cells.

9. A method according to claim 1, wherein said somatic tissue-specific stem cells are coupled with at least one liposome in a DNA-liposome complex.

10. A method according to claim 1, further comprising the step of incubating said egg to hatch.

11. A method according to claim 1, further comprising the step of raising said bird to at least an age at which said change in phenotype is expressed.

12. A method of altering the phenotype of a bird comprising introducing avian embryo cells into the air cell of an egg containing a bird during in ovo incubation, said embryo cells containing and capable of expressing at least one DNA molecule in an amount effective to cause a change in the phenotype of the bird.

13. A method according to claim 12, further comprising the step of transfecting said embryo cells with said DNA sequence prior to said introducing step.

14. A method according to claim 12 wherein said bird is selected from the group consisting of chickens, turkeys, ducks, geese, quail and pheasants.

15. A method according to claim 12 wherein said avian cells are introduced in ovo during about the last quarter of incubation.

16. A method according to claim 12, wherein said embryo cells are introduced in ovo at a stage of development in which said stem cells colonize tissue of said bird.

17. A method according to claim 12, wherein said embryo cells are coupled with at least one liposome in a DNA-liposome complex.

18. A method according to claim 12, wherein said embryo cells are primordial germ cells.

19. A method according to claim 12, wherein said embryo cells are embryonic stem cells.

20. A method according to claim 12, further comprising the step of incubating said egg to hatch.

21. A method according to claim 20, further comprising the step of raising said bird to at least an age at which said change in phenotype is expressed.

22. A method of altering the phenotype of a bird comprising introducing avian somatic tissue-specific stem cells to the air cell of an egg containing a bird during in ovo incubation, the avian somatic tissue-specific stem cells containing and capable of expressing at least one DNA molecule in an amount effective to cause a change in the phenotype of the bird.

23. A method according to claim 22, further comprising the step of transfecting said somatic tissue-specific stem cells with said DNA molecule prior to said introducing step.

24. A method according to claim 22 wherein said bird is selected from the group consisting of chickens, turkeys, ducks, geese, quail and pheasants.

25. A method according to claim 22 wherein said somatic tissue-specific stem cells are introduced in ovo during about the last quarter of incubation.

26. A method according to claim 22, wherein said embryo cells are introduced in ovo at a stage of development in which said stem cells colonize tissue of said bird.

27. A method according to claim 22, wherein said somatic tissue-specific stem cells are hematopoietic stem cells.

28. A method according to claim 22, wherein said somatic tissue-specific stem cells are neural crest stem cells.

29. A method according to claim 22, wherein said somatic tissue-specific stem cells are coupled with at least one liposome in a DNA-liposome complex.

30. A method according to claim 22, further comprising the step of incubating said egg to hatch.

31. A method according to claim 22, further comprising the step of raising said bird to at least an age at which said change in phenotype is expressed.

* * * * *